(12) United States Patent
Chen et al.

(10) Patent No.: US 12,396,903 B2
(45) Date of Patent: Aug. 26, 2025

(54) ANTI-STAIN ABSORPTION PAD FOR UNDERPANTS AND UNDERPANTS COMPRISING THE SAME

(71) Applicant: Artemis Medical Devices Co., Ltd., Kaohsiung (TW)

(72) Inventors: Yuan-Yi Chen, Kaohsiung (TW); Wen-Fei Shih, Kaohsiung (TW)

(73) Assignee: Artemis Medical Devices Co., Ltd., Kaohsiung (TW)

( * ) Notice: Subject to any disclaimer, the term of this patent is extended or adjusted under 35 U.S.C. 154(b) by 678 days.

(21) Appl. No.: 17/814,670

(22) Filed: Jul. 25, 2022

(65) Prior Publication Data
US 2023/0051812 A1   Feb. 16, 2023

(30) Foreign Application Priority Data
Aug. 10, 2021  (TW) .................................. 110209385

(51) Int. Cl.
*A61F 13/53*     (2006.01)
*A61F 13/534*    (2006.01)
*A61F 13/539*    (2006.01)

(52) U.S. Cl.
CPC ...... *A61F 13/53409* (2013.01); *A61F 13/539* (2013.01); *A61F 2013/53966* (2013.01)

(58) Field of Classification Search
CPC .................. A61F 13/53409; A61F 2013/53966
See application file for complete search history.

(56) References Cited

U.S. PATENT DOCUMENTS

| | | | | |
|---|---|---|---|---|
| 4,145,763 A * | 3/1979 | Abrams | ............... | A41D 13/129 2/403 |
| 4,280,230 A * | 7/1981 | LaFleur | .................. | A61F 13/70 2/408 |
| 4,338,939 A * | 7/1982 | Daville | ................. | A61F 5/4401 604/399 |
| 4,644,945 A * | 2/1987 | Thorner | ................ | A61F 5/4401 2/403 |
| 5,135,522 A * | 8/1992 | Fahrenkrug | ............. | A61F 13/64 604/401 |
| 5,435,014 A * | 7/1995 | Moretz | ............. | A61F 13/15699 2/403 |
| 5,549,593 A * | 8/1996 | Ygge | ...................... | A61F 13/72 604/391 |
| 5,669,902 A * | 9/1997 | Sivilich | ................. | A61F 13/471 604/397 |

(Continued)

*Primary Examiner* — Guy K Townsend (57) ABSTRACT

An anti-stain absorption pad for underpants and an underpants including the same are provided. The absorption pad includes a waterproof layer, at least one absorption layer and two fixing structures; wherein the waterproof layer includes a main body and two inverse-folded parts respectively provided at two opposite sides of the main body; the at least one absorption layer is disposed on the main body, and the at least one absorption layer is used for absorbing a liquid; and the two fixing structures are respectively disposed at the two inverse-folded parts, and fix the two inverse-folded parts on the at least one absorption layer. Therefore, in the present invention, since the fixing structures are covered by the waterproof layer due to the structure of the inverse-folded parts, backflow and secondary leakage of menstrual blood can be avoided, thereby achieving a complete leak-proof effect.

8 Claims, 8 Drawing Sheets

(56) References Cited

U.S. PATENT DOCUMENTS

| | | | | |
|---|---|---|---|---|
| 5,853,405 | A * | 12/1998 | Suprise | A61F 13/49413 604/385.29 |
| 6,807,685 | B1 * | 10/2004 | Hasegawa | A61F 13/505 2/400 |
| 7,344,526 | B2 * | 3/2008 | Yang | A61F 13/505 2/919 |
| 7,491,196 | B2 * | 2/2009 | Franke | A61F 13/496 604/397 |
| 7,875,014 | B2 * | 1/2011 | Hendren | A61F 13/565 604/396 |
| 7,993,322 | B2 * | 8/2011 | Brud | A61F 13/66 604/397 |
| 8,282,618 | B2 * | 10/2012 | Nordness | A61F 13/496 604/385.27 |
| 8,361,049 | B2 * | 1/2013 | Coenen | A61F 13/505 604/394 |
| 9,700,079 | B2 * | 7/2017 | Franke | A41B 9/001 |
| 10,165,801 | B2 * | 1/2019 | Blibech | A41B 9/02 |
| 10,478,351 | B2 * | 11/2019 | Alligood | A61F 13/474 |
| 11,950,988 | B2 * | 4/2024 | Alligood | A61F 13/476 |
| 2005/0131382 | A1 * | 6/2005 | Brud | A61F 13/66 604/401 |
| 2006/0206085 | A1 * | 9/2006 | Gegelys | A61F 13/471 604/395 |
| 2006/0243378 | A1 * | 11/2006 | Alberts | A61F 13/15739 156/204 |
| 2006/0247599 | A1 * | 11/2006 | Mullen | A61F 13/496 604/402 |
| 2016/0367410 | A1 * | 12/2016 | Alligood | A61F 13/47236 |
| 2019/0117471 | A1 * | 4/2019 | Brownlee | A61F 13/49017 |
| 2020/0085639 | A1 * | 3/2020 | Alligood | A61F 13/471 |
| 2022/0313502 | A1 * | 10/2022 | Brownlee | A61F 13/5519 |
| 2023/0051812 | A1 * | 2/2023 | Chen | A61F 5/44 |

* cited by examiner

ANTI-STAIN ABSORPTION PAD FOR UNDERPANTS AND UNDERPANTS COMPRISING THE SAME

CROSS-REFERENCE TO RELATED APPLICATION

This application claims the priority of Taiwanese patent application No. 110209385, filed on Aug. 10, 2021, which is incorporated herewith by reference.

BACKGROUND OF THE INVENTION

1. Field of the Invention

The present invention relates to an absorption pad and an underpants comprising the same, and more particularly, to an anti-stain absorption pad for underpants, which is applied in the structure of the underpants worn by women during the menstrual period for preventing leakage of menstrual blood, and an underpants comprising the same.

2. The Prior Arts

Absorption pad is a structure for absorbing liquid, which is generally disposed on the bottom of women's underpants for absorbing the menstrual blood generated during women's menstrual period, so as to prevent the menstrual blood from leaking and contaminating the clothes or bed sheets.

Conventional absorption pads are disposable and must be discarded after use. And, since the conventional absorption pads belong to non-recyclable waste and cannot be decomposed naturally, they must be processed by landfill treatment or incinerators, thereby causing the risk of generating toxic substances such as dioxin and polychlorinated biphenyls, which leads to serious environmental pollution. Therefore, the amount of garbage after a long time use will also cause a considerable burden to the environment.

In order to reduce the increasing amount of garbage, there are also period underwears on the market in which the structure of the underpants is designed to have waterproof function, or in which the underpants is provided with an absorption pad thereon so as to have the functions of barring and absorbing menstrual blood. However, in the structure of the conventional underpants, the absorption pad is fixed on the underpants in such a way that the absorption pad and the underpants are fixed together with sutures by means of general machine sewing or hand sewing, such that enables the conventional underpants to have functions of barring and absorbing menstrual blood. However, in the case of adopting such fixing way, since the sutures are mostly cotton yarn or made of other materials with water-absorbing function, when the menstrual blood is absorbed by the absorption pad, the sutures connecting the absorption pad and the underpants are prone to contact with the menstrual blood, such that a siphon phenomenon of the menstrual blood occurs at the suture, and causing the menstrual blood, which has flowed out and been absorbed by the absorption pad, to flow back via the sutures and contaminate the human body, thereby causing discomfort to the user. Also, when the menstrual blood is in an excessive amount, the menstrual blood flowing back from the fixing structures due to the siphon phenomenon may cause secondary leakage, thereby the conventional underpants cannot achieve a complete leakproof function.

In addition, for the structure of the conventional underpants, the sutures connecting the absorption pad and the underpants are prone to contact with the human skin after the underpants is worn for a long time, thereby, after long time contacting and rubbing, it is prone to cause discomfort to the human body, or even cause more severe circumstances such as skin abrasion or inflammation.

SUMMARY OF THE INVENTION

A primary objective of the present invention is to provide an anti-stain absorption pad for underpants, which is applied in the structure of the underpants worn by women during the menstrual period for preventing leakage of menstrual blood; and an underpants comprising the same.

Another objective of the present invention is to provide an anti-stain absorption pad for underpants, which prevents the human from rubbing their skin against the sutures when wearing the underpants, thereby improving the wearing touch and achieving a more comfortable wearing; and an underpants comprising the same.

For achieving the foregoing objectives, an anti-stain absorption pad for underpants, which comprises a waterproof layer, at least one absorption layer and two fixing structures, is provided in the present invention.

The waterproof layer comprises a main body and two inverse-folded parts, wherein the main body includes a first surface and a second surface, the two inverse-folded parts are respectively provided at two opposite sides of the main body, and each of the two inverse-folded parts includes a third surface and a fourth surface.

The at least one absorption layer includes a first absorption surface and a second absorption surface, the at least one absorption layer is disposed on the main body, the first absorption surface is arranged on the second surface of the waterproof layer, the third surfaces of the two inverse-folded parts are arranged on the second absorption surface, and the at least one absorption layer is used for absorbing a liquid.

The two fixing structures are respectively disposed at the two inverse-folded parts, and fix the two inverse-folded parts on the at least one absorption layer.

In some embodiments, each of the two inverse-folded parts further comprises a folded portion, each of the folded portions includes a fifth surface and a sixth surface, and the two fixing structures respectively penetrate through the fifth surface, the sixth surface, the fourth surface, the third surface, the second absorption surface, and the first absorption surface in sequence.

In some embodiments, an underpants comprising the aforementioned anti-stain absorption pad is provided, wherein the underpants comprises a front crotch part and a rear crotch part, and two opposite sides of the waterproof layer are connected to the front crotch part and the rear crotch part, respectively.

In some embodiments, the underpants further comprises a bottom crotch part, two opposite sides of the bottom crotch part are connected to the front crotch part and the rear crotch part, respectively, and the first surface of the waterproof layer is located adjacent to the bottom crotch part.

In some embodiments, the underpants further comprises a bottom crotch part, two opposite sides of the bottom crotch part are connected to the front crotch part and the rear crotch part, respectively, and the first surface of the waterproof layer is disposed on the bottom crotch part.

In some embodiments, an underpants comprising the aforementioned anti-stain absorption pad is provided, wherein the underpants comprises a front crotch part, a rear crotch part and a bottom crotch part, and the first surface of the waterproof layer is disposed on the bottom crotch part and the rear crotch part.

In some embodiments, the anti-stain absorption pad for underpants comprises a plurality of the absorption layers.

In some embodiments, the two fixing structures are sutures.

The effects of the present invention are in those, since the fixing structures can be covered by the waterproof layer due to the structure of the inverse-folded parts, it is possible to prevent the liquid from flowing back via the fixing structures due to the siphon phenomenon and contaminating the human body, thereby causing discomfort to the user. Also, when the menstrual blood is in an excessive amount, it is possible to avoid the secondary leakage caused by the menstrual blood flowing back from the fixing structures due to the siphon phenomenon, thereby achieving a complete leakproof effect.

In addition, in the present invention, the fixing structures can be covered by the waterproof layer, which prevents the human skin from contacting with and rubbing against the fixing structures for a long time when the user wears the underpants, thereby improving the wearing touch and achieving a more comfortable wearing.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The following description provides a further understanding of the embodiments of the present invention in conjunction with the drawings and the reference numerals, in order that those skilled in the art can implement them after studying the present specification.

Figure 1:
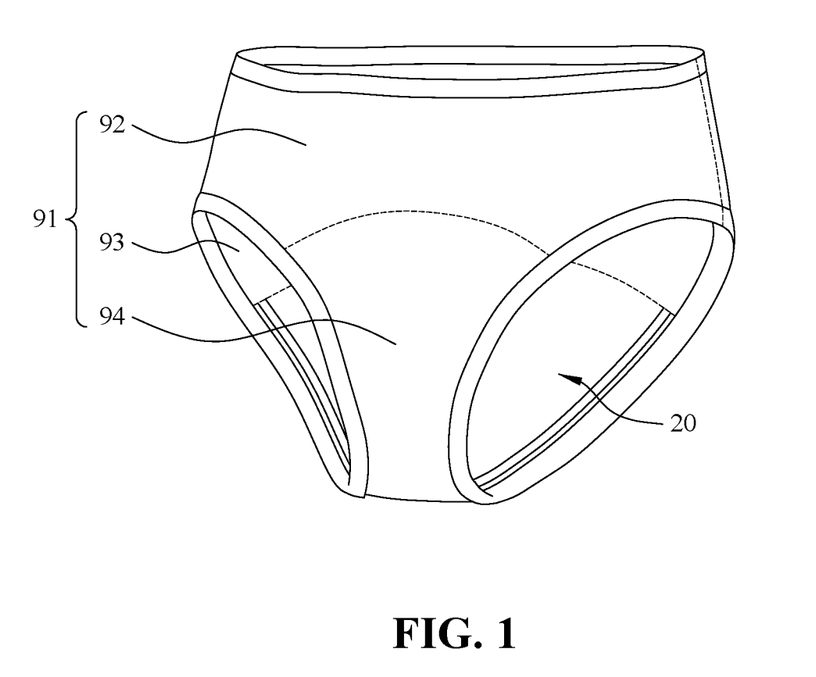
FIG. 1 is a perspective view of an anti-stain absorption pad for underpants according to a first embodiment of the present invention.
Figure 2:
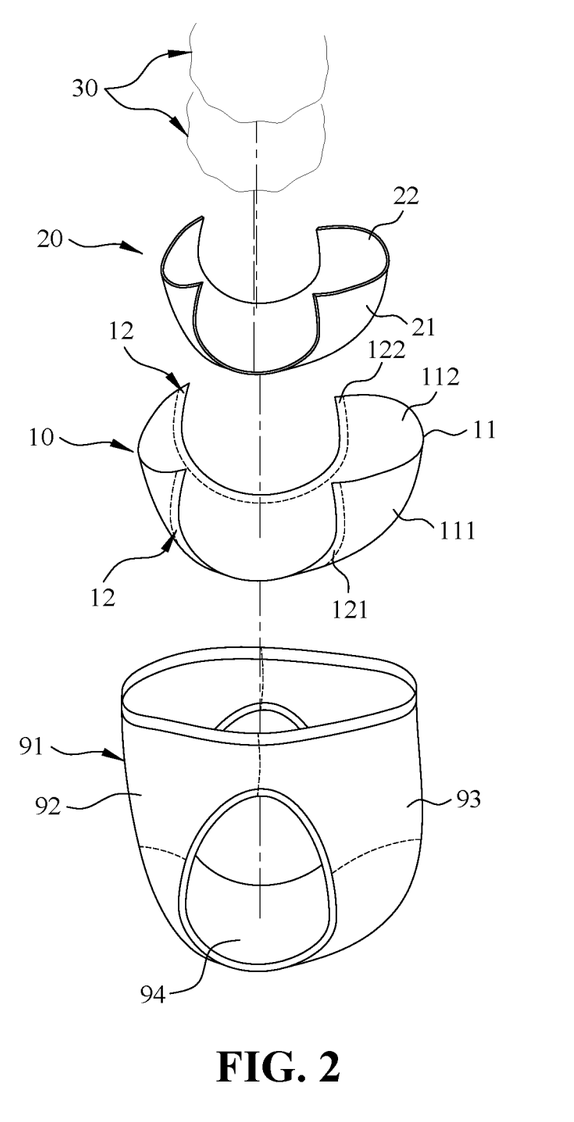
FIG. 2 is an exploded view of the anti-stain absorption pad for underpants according to the first embodiment of the present invention.
Figure 3:
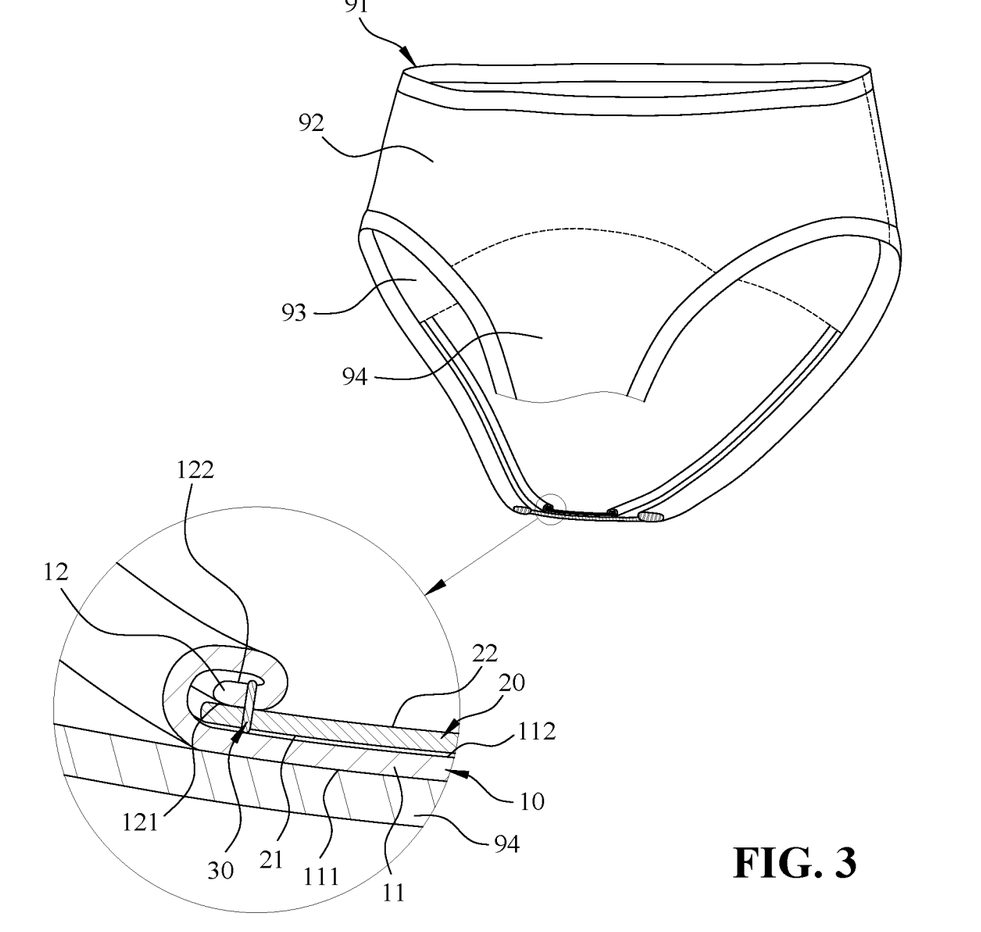
FIG. 3 is a cross-sectional view of the anti-stain absorption pad for underpants according to the first embodiment of the present invention.

FIG. 1 is a perspective view of an anti-stain absorption pad for underpants according to a first embodiment of the present invention. FIG. 2 is an exploded view of the anti-stain absorption pad for underpants according to the first embodiment of the present invention. FIG. 3 is a cross-sectional view of the anti-stain absorption pad for underpants according to the first embodiment of the present invention. As shown in FIGS. 1 to 3, an anti-stain absorption pad for underpants, which comprises a waterproof layer 10, at least one absorption layer 20 and two fixing structures 30, is provided in the present invention.

The waterproof layer 10 comprises a main body 11 and two inverse-folded parts 12, wherein the main body 11 includes a first surface 111 and a second surface 112. The two inverse-folded parts 12 are respectively provided at two opposite sides of the main body 11, and each of the two inverse-folded parts 12 includes a third surface 121 and a fourth surface 122. Specifically, in the first embodiment of the present invention, the main body 11 is in a shape of sheet, and the bottom and top surfaces of the main body 11 are respectively defined as the first surface 111 and the second surface 112, the two inverse-folded parts 12 are respectively provided at the two opposite sides of the main body 11, and the bottom and top surfaces of each of the two inverse-folded parts 12 are respectively defined as the third surface 121 and the fourth surface 122.

The first surface 111 of the main body 11 is continued with the third surfaces 121 of the two inverse-folded parts 12, and the second surface 112 of the main body 11 is continued with the fourth surfaces 122 of the two inverse-folded parts 12. However, the arrangement of the first surface 111, the second surface 112, the third surface 121 and the fourth surface 122 is not limited thereto, and can be changed according to requirements. For example, the first surface 111 of the main body 11 can be continued with the four surfaces 122 of the two inverse-folded parts 12, and the second surface 112 of the main body 11 can be continued with the third surfaces 121 of the two inverse-folded parts 12.

Preferably, the main body 11 is in a shape of rectangle in which two long sides of the rectangle are concave inward to fit the curvature of the inner thigh of the human body, such that the main body 11 can provide fitter and more comfortable wearing.

Preferably, in the first embodiment of the present invention, the waterproof layer 10 is made of a waterproof fabric with functions of waterproof, breathability, windbreak and/or thermal wearing. However, the function of the waterproof layer 10 is not limited thereto, and can be changed according to requirements.

Figure 4:
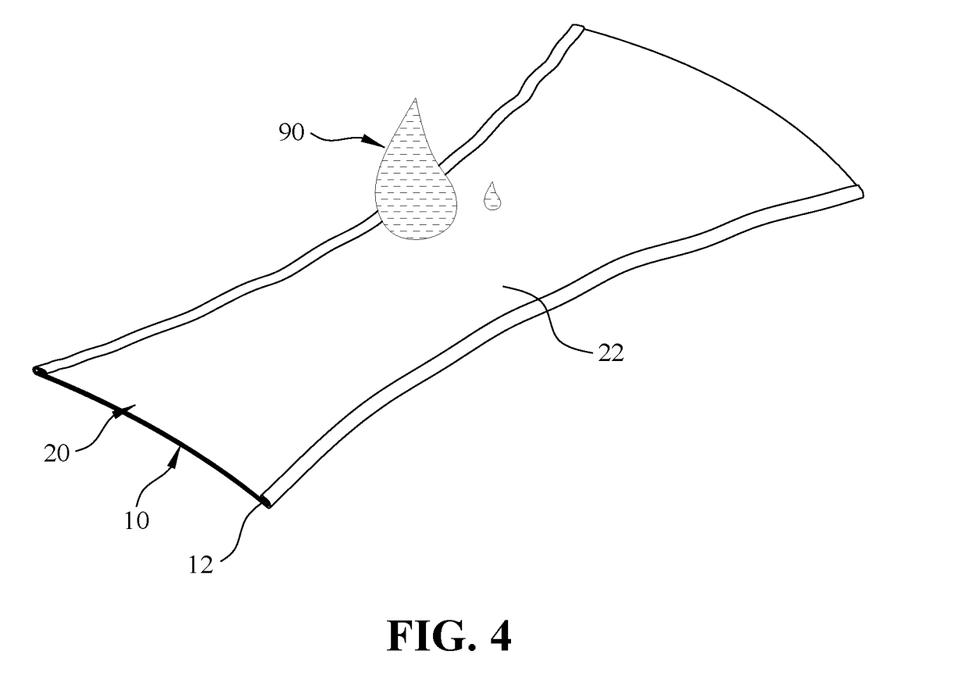
FIG. 4 is a schematic diagram illustrating the liquid absorption of the anti-stain absorption pad for underpants according to a first embodiment of the present invention.

The at least one absorption layer 20 includes a first absorption surface 21 and a second absorption surface 22. The at least one absorption layer 20 is disposed on the main body 11. The first absorption surface 21 of the at least one absorption layer 20 is arranged on the second surface 112 of the waterproof layer 10. The third surfaces 121 of the two inverse-folded parts 12 are arranged on the second absorption surface 22. The at least one absorption layer 20 is used for absorbing a liquid 90 (as shown in FIG. 4).

Specifically, in the first embodiment of the present invention, the at least one absorption layer 20 is in a shape of sheet, and the bottom and top surfaces of the at least one absorption layer 20 are respectively defined as the first absorption surface 21 and the second absorption surface 22, and the first absorption surface 21 of the at least one absorption layer 20 is arranged on the second surface 112 of the waterproof layer 10.

Referring to FIG. 3, preferably, the at least one absorption layer 20 is in a shape of rectangle, and the overall size of the at least one absorption layer 20 is equal to or slightly smaller than the overall size of the waterproof layer 10, such that the waterproof layer 10 can be inversely folded at two opposite sides along two opposite sides of the at least one absorption layer 20, respectively, thereby the third surfaces 121 of the two inverse-folded parts 12 are arranged on the second absorption surface 22 of the at least one absorption layer 20.

Both the first absorption surface 21 and the second absorption surface 22 of the at least one absorption layer 20 can be used for absorbing the liquid 90. However, the structure of the absorption layer 20 is not limited thereto, and can be changed to a structure wherein only one of the absorption surfaces has the function of absorbing the liquid 90 according to requirements.

In the first embodiment of the present invention, there is only one absorption layer 20. However, the number of the absorption layer 20 is not limited thereto, and can be increased according to requirements. For example, a plurality of absorption layers 20 can be provided on the waterproof layer 10, so as to increase the effect of the anti-stain absorption pad for underpants in terms of absorbing the liquid 90.

The two fixing structures 30 are respectively disposed at the two inverse-folded parts 12, and fix the two inverse-folded parts 12 on the at least one absorption layer 20. In the first embodiment of the present invention, the two fixing structures 30 are respectively sutures, wherein the sutures are used to fix the two inverse-folded parts 12 and the at least one absorption layer 20 together by means of hand sewing or machine sewing.

Specifically, in the first embodiment of the present invention, the two fixing structures 30 respectively penetrate through the fourth surface 122 of the two inverse-folded parts 12, the third surface 121 of the two inverse-folded parts 12, the second absorption surface 22 of the absorption layer 20, and the first absorption surface 22 of the absorption layer 20 in sequence, thereby fixing the waterproof layer 10 and the absorption layer 20 together.

In the first embodiment of the present invention, an underpants 91 comprising the aforementioned anti-stain absorption pad is further provided. The underpants 91 comprises a front crotch part 92, a rear crotch part 93 and a bottom crotch part 94. Two opposite sides of the bottom crotch part 94 are respectively connected to the front crotch part 92 and the rear crotch part 93, the waterproof layer 10 is disposed on the bottom crotch part 94, and the first surface 111 of the main body 11 of the waterproof layer 10 is fixed on the bottom crotch part 94. In this way, when the underpants 91 is worn, the liquid 90 can be absorbed by the second absorption surface 22 of the absorption layer 20. In the first embodiment of the present invention, the liquid 90 is menstrual blood, but the liquid 90 to be absorbed is not limited thereto.

Specifically, the first surface 111 of the main body 11 of the waterproof layer 10 can be attached to the bottom crotch part 94 of the underpants 91 by means of adhering or sewing, such that the first surface 111 of the main body 11 of the waterproof layer 10 can completely fit the bottom crotch part 94 of the underpants 91. However, the disposing position of the waterproof layer 10 on the underpants 91 is not limited thereto. The waterproof layer 10 can be further disposed on the rear crotch part 93 of the underpants 91, or further disposed on the front crotch part 92 and the rear crotch part 93 of the underpants 91 simultaneously.

Referring to FIGS. 3 and 4, wherein FIG. 4 is a schematic diagram illustrating the use of the anti-stain absorption pad for underpants according to a first embodiment of the present invention. When there is liquid 90 flowing to the absorption layer 20, the liquid 90 will be absorbed by the second absorption surface 22 of the absorption layer 20. When the liquid 90 is in an excessive amount and thus flows from the second absorption surface 22 to the first absorption surface 21 of the absorption layer 20, since the waterproof layer 10 is provided at the outer side of the first absorption surface 21 of the absorption layer 20, it is possible to prevent the liquid 90 from further infiltrating into the bottom crotch part 94 of the underpants 91, thereby avoiding the leakage of the liquid 90 and achieving the anti-stain effect.

It is noted that in the present invention, since the fixing structures 30 are covered by the waterproof layer 10 due to the structure of the inverse-folded parts 12, even if the liquid 90 is absorbed by the fixing structures 30 due to the siphon phenomenon, the human body can be prevent from contacting with the liquid 90 flowing back along the fixing structures 30, thereby achieving a cleaner effect. Also, this prevents the circumstance in the conventional fixing structures 30 that the liquid 90 from flowing back to the absorption layer 20 due to the siphon phenomenon, thereby causing discomfort to the human body arisen from contacting with the liquid 90 and causing the leakage of the liquid 90.

In addition, since the fixing structures 30 are covered by the waterproof layer 10, when the user wears the underpants, the human skin can be prevent from contacting with and rubbing against the fixing structures 30 for a long time, thereby a more comfortable wearing touch and a simple and aesthetic appearance can be achieved.

Figure 5:
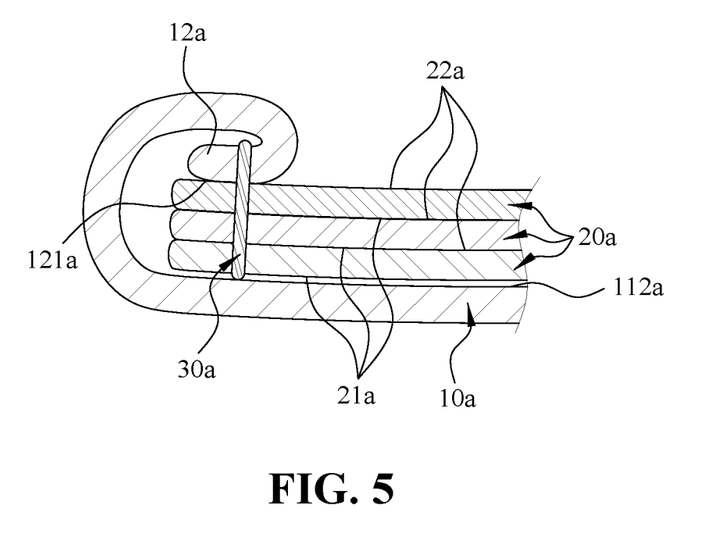
FIG. 5 is a cross-sectional view of an anti-stain absorption pad for underpants according to a second embodiment of the present invention.

FIG. 5 is a cross-sectional view of an anti-stain absorption pad for underpants according to a second embodiment of the present invention. As shown in FIG. 5, in the present invention, the second embodiment is different from the first embodiment in that the anti-stain absorption pad for underpants comprises a plurality of absorption layers 20. The plurality of absorption layers 20 (for example, three absorption layers 20) are disposed on the waterproof layer 10. The second absorption surface 22a of the topmost absorption layer 20a faces upward, and the first absorption surface 21a of the topmost absorption layer 20a is arranged on the second absorption surface 22a of another absorption layer 20a. The first absorption surface 21a of the middle absorption layer 20a is arranged on the second absorption surface 22a of the bottommost absorption layer 20a. The first absorption surface 21a of the bottom absorption layer 20a is located adjacent to the second surface 112a of the waterproof layer 10a. The waterproof layer 10a are inversely folded at two opposite sides thereof, such that the third surfaces 121a of the two inverse-folded parts 12a are arranged on the second surface 22a of the topmost absorption layer 20a. In this way, the effect of the anti-stain absorption pad for underpants in terms of absorbing the liquid 90 can be increased.

Figure 6:
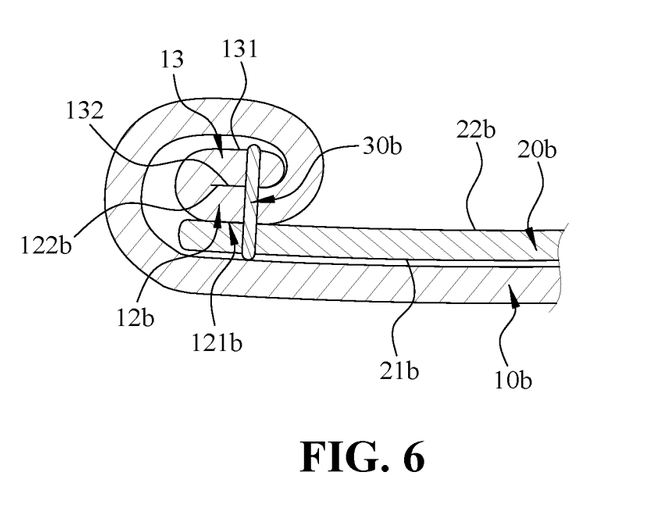
FIG. 6 is a cross-sectional view of an anti-stain absorption pad for underpants according to a third embodiment of the present invention.

FIG. 6 is a cross-sectional view of an anti-stain absorption pad for underpants according to a third embodiment of the present invention. As shown in FIG. 6, in the present invention, the third embodiment is different from the first embodiment in that each of the two inverse-folded parts 12b further include a folded portion 13, and the bottom and top surfaces of each of the folded portions 13 are respectively defined as a fifth surface 131 and a sixth surface 132. Preferably, the fifth surface 131 is continued with the third surface 121b, and the sixth surface 132 is continued with the fourth surface 122b.

The two fixing structures 30b respectively penetrate through the fifth surface 131, the sixth surface 132, the fourth surface 122b, the third surface 121b, the second absorption surface 22b and the first absorption surface 21b in sequence. In this way, the effect of fixing the waterproof layer 10b and the absorption layer 20b together can be increased, and the effect of providing the fixing structures 30b can be further enhanced, that is, this prevent the waterproof layer 10b from being separated from the absorption layer 20b due to the breakage of the inverse-folded parts 12b.

Figure 7:
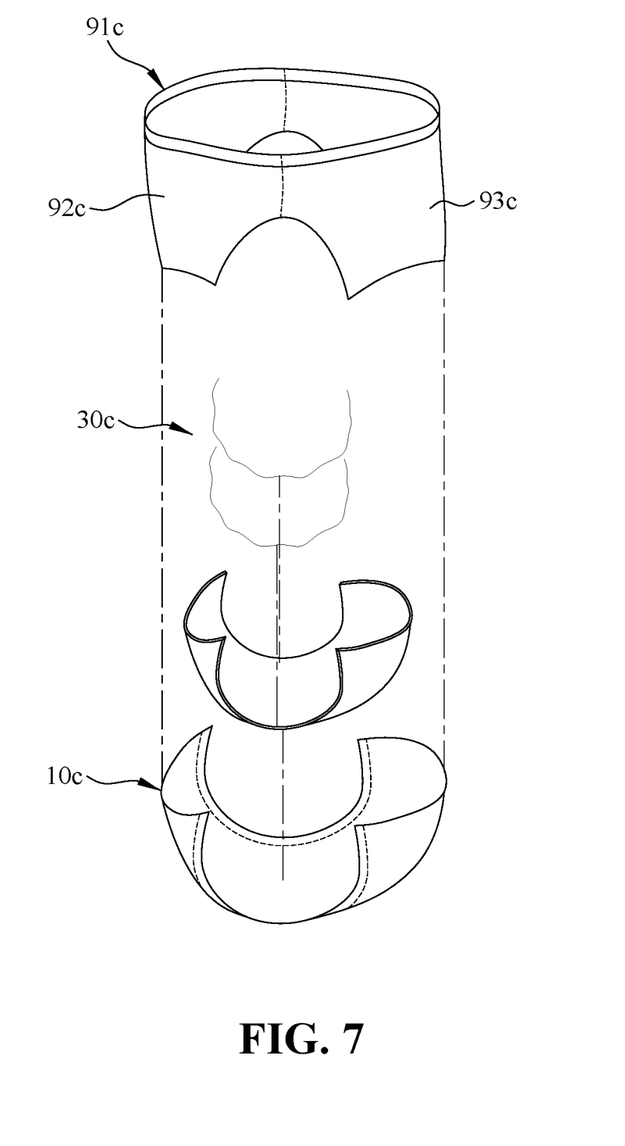
FIG. 7 is an exploded view of an anti-stain absorption pad for underpants according to a fourth embodiment of the present invention.

FIG. 7 is an exploded view of an anti-stain absorption pad for underpants according to a fourth embodiment of the present invention. As shown in FIG. 7, in the present invention, the fourth embodiment is different from the first embodiment in that the underpants 91c only includes a front crotch part 92c and a rear crotch part 93c, and two opposite sides of the waterproof layer 10c are respectively connected to the front crotch part 92c and rear crotch part 93c. In this way, it is possible to avoid the stuffiness caused by the underpants 91c with a excessive thickness, thereby achieving a better breathable effect.

Figure 8:
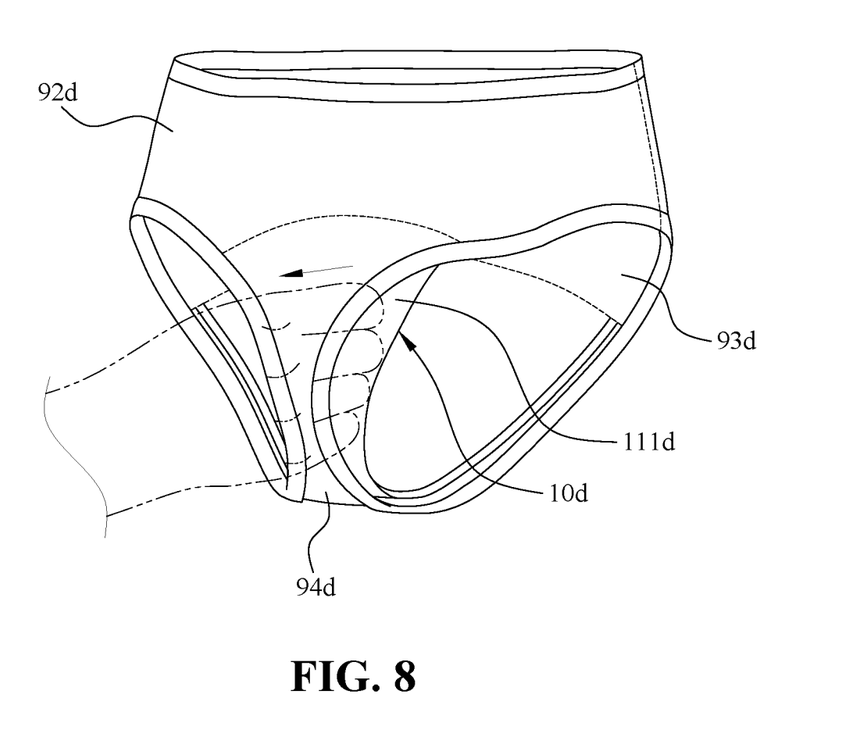
FIG. 8 is a perspective view of an anti-stain absorption pad for underpants according to a fifth embodiment of the present invention.

FIG. 8 is a perspective view of an anti-stain absorption pad for underpants according to a fifth embodiment of the present invention. As shown in FIG. 8, in the present invention, the fifth embodiment is different from the first embodiment in that only two opposite sides of the waterproof layer 10d are respectively connected to the front crotch part 92d and the rear crotch part 93d, while the first surface 111d of the waterproof layer 10d is separated from and not fixedly attached to the bottom crotch part 94d. In this way, it is more convenient for the user to perform cleaning.

In the embodiments of the present invention, the underpants 91 is briefs. However, the type of the underpants 91 is not limited thereto, and can be changed to boxers or other types of underpants according to requirements.

As described above, in the present invention, since the fixing structures 30 are covered by the waterproof layer 10 due to the structure of the inverse-folded parts 12, it is possible to prevent the liquid 90 from flowing back via the fixing structures 30 due to the siphon phenomenon and contaminating the human body, thereby causing discomfort to the user. Also, when the menstrual blood is in an excessive amount, it is possible to prevent the secondary leakage caused by the menstrual blood flowing back from the fixing structures 30 due to the siphon phenomenon, thereby achieving a complete leakproof effect.

In addition, in the present invention, the fixing structures 30 can be covered by the waterproof layer 10, which prevents the human skin from contacting with and rubbing against the fixing structures 30 for a long time when the user wears the underpants, thereby improving the wearing touch and achieving a more comfortable wearing touch.

The above descriptions are only provided to explain the preferred embodiments of the present invention, it is not intended to limit the present invention in any form. Therefore, any modifications and changes made without departing from the spirit of the present invention should be included within the scope as claimed in the present invention.

What is claimed is:

1. An anti-stain absorption pad for underpants, comprising:
   a waterproof layer comprising a main body and two inverse-folded parts, wherein the main body includes a first surface and a second surface, the two inverse-folded parts are respectively provided at two opposite sides of the main body, and each of the two inverse-folded parts includes a third surface and a fourth surface;
   at least one absorption layer comprising a first absorption surface and a second absorption surface, wherein the at least one absorption layer is disposed on the main body, the first absorption surface is arranged on the second surface of the waterproof layer, the third surfaces of the two inverse-folded parts are arranged on the second absorption surface, and the at least one absorption layer is used for absorbing a liquid; and
   two fixing structures, which are respectively disposed at the two inverse-folded parts, and fix the two inverse-folded parts on the at least one absorption layer.

2. The anti-stain absorption pad for underpants according to claim 1, wherein each of the two inverse-folded parts comprises a folded portion, each of the folded portions includes a fifth surface and a sixth surface, and the two fixing structures respectively penetrate through the fifth surface, the sixth surface, the fourth surface, the third surface, the second absorption surface, and the first absorption surface in sequence.

3. An underpants comprising the anti-stain absorption pad according to claim 1, wherein the underpants comprises a front crotch part and a rear crotch part, and two opposite sides of the waterproof layer are connected to the front crotch part and the rear crotch part, respectively.

4. The underpants according to claim 3, wherein the underpants further comprises a bottom crotch part, two opposite sides of the bottom crotch part are connected to the front crotch part and the rear crotch part, respectively, and the first surface of the waterproof layer is located adjacent to the bottom crotch part.

5. The underpants according to claim 3, wherein the underpants further comprises a bottom crotch part, two opposite sides of the bottom crotch part are connected to the front crotch part and the rear crotch part, respectively, and the first surface of the waterproof layer is disposed on the bottom crotch part.

6. An underpants comprising the anti-stain absorption pad according to claim 1, wherein the underpants comprises a front crotch part, a rear crotch part and a bottom crotch part, and the first surface of the waterproof layer is disposed on the bottom crotch part and the rear crotch part.

7. The anti-stain absorption pad for underpants according to claim 1, comprising a plurality of the absorption layers.

8. The anti-stain absorption pad for underpants according to claim 1, wherein the two fixing structures are sutures.

\* \* \* \* \*